United States Patent
Boehringer et al.

(10) Patent No.: US 7,686,785 B2
(45) Date of Patent: Mar. 30, 2010

(54) MEDICAL SUCTION CONTROL WITH ISOLATION CHARACTERISTICS

(75) Inventors: John R. Boehringer, Wynnewood, PA (US); John Karpowicz, Chester Springs, PA (US); Kevin Klocek, Wynnewood, PA (US); Michael Kauffmann, Drexel Hill, PA (US)

(73) Assignee: Boehringer Laboratories, Incorporated, Norristown, PA (US)

( * ) Notice: Subject to any disclaimer, the term of this patent is extended or adjusted under 35 U.S.C. 154(b) by 0 days.

(21) Appl. No.: 11/827,628

(22) Filed: Jul. 12, 2007

(65) Prior Publication Data

US 2008/0015504 A1  Jan. 17, 2008

Related U.S. Application Data

(60) Provisional application No. 60/830,636, filed on Jul. 13, 2006.

(51) Int. Cl.
 *A61M 1/00* (2006.01)
(52) U.S. Cl. .................................................... 604/119
(58) Field of Classification Search .................. 604/73, 604/119
 See application file for complete search history.

(56) References Cited

U.S. PATENT DOCUMENTS

| | | | | |
|---|---|---|---|---|
| 4,468,226 A | * | 8/1984 | Kurtz et al. | 604/321 |
| 5,730,727 A | * | 3/1998 | Russo | 604/118 |
| 6,024,120 A | * | 2/2000 | Yam et al. | 137/495 |
| 6,070,582 A | * | 6/2000 | Kee | 128/207.16 |
| 6,368,310 B1 | * | 4/2002 | Bemis et al. | 604/319 |
| 6,673,055 B2 | * | 1/2004 | Bemis et al. | 604/319 |
| 6,695,823 B1 | * | 2/2004 | Lina et al. | 604/304 |
| 6,749,592 B2 | * | 6/2004 | Lord | 604/319 |
| 6,755,807 B2 | * | 6/2004 | Risk et al. | 604/319 |
| 6,955,664 B2 | * | 10/2005 | D'Antonio | 604/323 |
| 7,175,612 B2 | * | 2/2007 | Felix et al. | 604/323 |
| 2003/0014022 A1 | * | 1/2003 | Lockwood et al. | 604/315 |
| 2004/0261792 A1 | * | 12/2004 | Wolf et al. | 128/203.15 |
| 2005/0124966 A1 | * | 6/2005 | Karpowicz et al. | 604/500 |
| 2007/0219532 A1 | * | 9/2007 | Karpowicz et al. | 604/540 |

* cited by examiner

*Primary Examiner*—Nicholas D Lucchesi
*Assistant Examiner*—Aarti B Berdichevsky
(74) *Attorney, Agent, or Firm*—RatnerPrestia (57) ABSTRACT

A suction regulator for controlling a level of negative pressure in a system in which compensatory clean airflow is used to isolate a control device for regulating suction delivered to a patient is disclosed. The regulator comprises an inlet; an outlet; a controller for controlling the suction delivered to the inlet; and a barrier for isolating the controller from the inlet.

19 Claims, 4 Drawing Sheets

SECTION A-A

MEDICAL SUCTION CONTROL WITH ISOLATION CHARACTERISTICS

CROSS REFERENCE TO RELATED APPLICATIONS

This application claims the benefit of the filing date of the provisional application entitled "MEDICAL SUCTION CONTROL WITH ISOLATION CHARACTERISTICS" filed Jul. 13, 2006 and assigned Ser. No. 60/830,636, the contents of which are incorporated herein by reference.

FIELD OF THE INVENTION

The disclosed invention relates to devices and methods of creating a medical suction control mechanism that is tolerant to gases, liquids, aerosols, and suspensions entering the suction regulator control mechanism without a deleterious impact on control performance.

BACKGROUND OF THE INVENTION

Suction controls are routinely used in hospitals to regulate the level of suction delivered from a central supply system to the patient. Patient safety requires the high vacuum from the central supply be regulated to a lower safe level and adjustable for any number of clinical needs. On its most basic level, suction is used to remove fluids and debris from body cavities and is employed in virtually any location where a patient is present. Modern hospitals employ central suction systems with distributed supply at the patient bed. Mechanical controls reduce the high vacuum levels present in the central suction system to lower levels safe for patients and suitable for the patient collection devices. Collection devices are typically plastic, disposable devices that are used to accumulate fluids and debris. The collection devices are located between the point of collection and the control device and serve to protect the piping system and manual controls from contamination by bodily substances.

The suction control mechanism that interfaces high vacuum in the central suction system with the patient contact collection systems are typically reusable mechanical devices. Though application of suction to patients generally results in dedicated one way flow of material away from the patient, there are clinical applications such as drainage from the stomach that necessitate periodic relief of vacuum pressures while in contact with patient.

Unlike other fluidic systems in the hospital, such as oxygen, nitrogen, or medical air, the inlet to the suction system is proximal to the patient and may not be filtered. Typical hospital suction systems utilize a canister to act as a fluidic trap. This canister is typically located between the patient and the suction control. In addition to providing gravimetric or centrifugal separation of liquids and gases, this canister may contain a mechanical float and/or hydrophobic membrane to handle an overflow condition. The failure to use a canister or the failure of the internal overflow mechanisms of the canister may also cause liquids, solids, and suspensions to enter the suction control and hospital suction system.

In addition to room air, caregivers may introduce foreign material or fluids into the flow path. This foreign material may include, singly or in combination:
  Vapors
  Aerosols
  Caustic and or Acidic fluids
  Dust, lint and fine particulate matter
  Liquids
  Solids
  Suspensions containing solids/liquid components
  Microorganisms Any failure of the hospital collection system, such as an overfilled canister, perforated hydrophobic membrane, or sticking gravity float, will cause foreign material to enter the suction regulator. Incorrect setup of the patient collection circuit or unintentional acts by the caregiver can also bypass these safety measures.

Any foreign material that enters the internal flow path of a suction control can affect the system's ability to properly regulate the high levels of suction delivered from the central suction system to clinically safe levels. Infiltration of foreign matter can also render the system inoperable.

Some overflow systems fail to restrict the entry of aerosols into the suction control. These aerosol mixtures may bypass the safety mechanisms of the canister system and find their way to the operable parts of the suction control where the buildup may lead to degradation in the performance of the suction control.

A typical failure mode of a suction regulator is for a bolus of biological fluid to be aspirated into the regulator by accident, followed by a period where low relative humidity room air is drawn in. The dry air flow causes the fluid to dry out resulting in a sticky coating covered with lint and dust. Over time if not properly serviced, these accumulations progress until, layer by layer, system performance is compromised or the system may be disabled.

Filters are used to effectively control aerosols from entering controls, but filters have the limitation of becoming progressively occluded with particles and liquids and require frequent replacement in order to maintain acceptable flow levels. Filters also do not fail in a safe mode in that when clogged, the regulator may indicate that suction is being applied to the patient when in fact the clogged filter is preventing the application of suction to the patient. The failure to apply suction, especially in an emergency is a risk associated with medical suction controls.

Suction systems in the hospital pose five distinct risks to patient safety

1. Application of excessive levels of suction (>300 mmHg) can rapidly precipitate localized barotraumas where the suction has been applied to the patient.
2. Mildly excessive suction, above normal venous return pressures (150 mmHg-300 mmHg) can limit tissue perfusion causing localized tissue necrosis during prolonged application.
3. The inability to deliver adequate static pressure and flow can limit a caregiver's ability to remove blood and vomitus from a patient's oral pharanx and establish a patent airway during emergency procedures.
4. The failure of an intermitting suction circuit in nasogastric procedures to cycle on and off can expose the lining of the stomach to continuous suction and localized barotraumas. Over extended periods of time, this continuous suction will erode the protective lining of the stomach resulting in ulcerations in the highly vascularized tissues.
5. The inability of a regulator to maintain a stable regulated vacuum characterized by two conditions: Drift, a tendency for the set-point to change over time; and Spike, the tendency to apply significantly greater levels of suction pressure as flow is restricted due to the contact with tissue in the patient catheter, either of these two conditions will prevent the physician prescribed level of suction from being applied to the patient.

The most common cause of failure in hospital suction controls is the entrance of foreign material into the regulation mechanism of the circuit. Therefore, in the interests of reliability and performance there is a need to limit or prevent foreign materials from entering the pressure regulation mechanism of a suction control apparatus.

SUMMARY OF THE INVENTION

Suction regulators are typically constructed to provide adjustable suction levels based on individual clinical requirements. Suction regulators generally utilize a control mechanism that is composed of a spring and diaphragm, which actuates a sealing mechanism. The diaphragm provides an atmospheric pressure reference and a driving force for actuating the sealing mechanism. A spring counteracts the atmospheric reference and provides a specific suction output. By varying the amount of spring force exerted, different suction pressures may be delivered to the patient circuit. The sealing mechanism is commonly an elastomeric seal in proximate sealing location to a surface. An analogous construction would employ a bellows that provides the same functionality as a spring and diaphragm.

An exemplary suction regulator according to the present invention includes an inlet and outlet for attachment to the patient and a source of suction; a control mechanism for sensing and controlling the suction pressure output; a gauge for indicating the controlled output and specific mechanical construction features for ensuring some important fluidic functions. Specifically, these features are directed at performance issues such as dampening vibration and ensuring that the controlled output tracks the set-point accurately in spite of changes that occur in the suction delivery circuit due to changes in fluid resistance and flow.

Suction control mechanisms typically provide a means of "sensing" the delivered suction pressure and making adjustments to the sealing mechanism as changes to conditions in the collection circuit occur. The 'sensing' function is accomplished by allowing a feedback signal of air or fluid to communicate with the sensing side of the diaphragm. This feedback traditionally exposes the control mechanism to the aforementioned list of foreign materials introduced into the circuit. In prior art regulators the feedback signal is directed through a passage of controlled dimensional characteristics for purposes of specific regulator performance and therefore could be affected by foreign materials.

The volume of air displaced by the diaphragm and spring during their normal functioning creates a pumping effect in relation to the air space inside of the regulated circuit. To build a regulator capable of high flow, with minimal variation in its regulated setting across various flow regimes, it is important to have a large diaphragm and low spring rate to maximize the distance the control mechanism needs to travel. This pumping effect may also draw unwanted foreign materials into the more critical areas of the suction control device.

The invention described herein isolates the critical areas of the regulator by the use of a dedicated air flow or "curtain" and a mechanical shroud means. An alternate embodiment illustrates isolation via the placement of a diaphragm proximal to the sealing mechanism. This isolation protects the critical feedback passage from contamination while maintaining the critical performance characteristics.

The air curtain function described in this submission allows a controlled flow of air to travel through the regulator mechanism providing for a clean air wash through the feedback signal passage of the regulator. This air-flow is substantially small enough to not alter the set point of the regulator (typically less than 1000 cc/min). The flow rate being controlled may be up to 250 liters per minute. According to an exemplary embodiment of the invention, the air flow rate may be about 0.1% to about 10% of the maximum flow rate through the fluid passageway (e.g., 250 liters per minute). The clean air wash travels through passages that are sufficiently small enough to encourage the relative velocity of this airflow to be sufficiently high to shield the underlying components from intrusion by foreign material. The clean air wash also creates an air bearing effect to minimize frictional forces between moving parts, thus improving spike and drift performance.

The controlled airflow provides a one-way flow from the sensing side of the diaphragm through the feedback signal passage towards the sealing mechanism. This one-way flow velocity prevents the incursion of contaminating materials and is sufficient to counteract the pumping effect counter velocity caused by any retraction of the diaphragm.

A mechanical shroud covers any exposed surfaces and creates a labyrinth that serves to prevent incoming foreign matter from adhering to the working parts of the regulator. The accumulation of liquids or solids on the movable parts of the suction control can affect response, dead band and overall performance. In severe cases, the functional elements become bonded together resulting in complete loss of regulation.

The internal flow passages of the regulator can be configured with geometry capable of causing liquids and aerosolized particles to be diverted away from the control aspects of the regulator. Geometry capable of causing a vortex can create centrifugal forces capable of moving heavier fluids to the outside of the flow path, while allowing the regulation means to operate inside of the flow path and free of contaminating materials.

An alternative embodiment to the isolation provided by the air curtain and/or the mechanical shroud is the isolation of the control features from the regulated suction by using a diaphragm immediately adjacent to the sealing means portion of the control. A diaphragm placed in such a manner would communicate changes in the regulated suction circuit to the control region of the regulator and the control features would control the passage of atmospheric air to achieve desired performance parameters. Alternately, a bellows could be configured in a similar fashion. Each of these alternative approaches include a damping means to minimize oscillation of an otherwise low friction, high sensitivity feedback regulating system.

It may also be desirable from a maintenance standpoint to regularly flush clean water, or a cleaning agent through the internal mechanism of a suction regulator in an attempt to dislodge any accumulated foreign matter. This may be done to remove accumulated debris or to prepare the unit for disinfection or sterilization. Present suction regulation mechanisms cannot be cleaned in this manner without trapping fluid within the internal control regulator. Cleaning agents that are not properly removed from the working components of the regulator may lead to the degradation of performance over time. The present invention allows for this flushing method without the accumulation of fluid inside of the unit, an important and unique advantage.

Regulators utilizing a spring-opposed diaphragm will maintain a given suction pressure in response to flow demands on the system. In a static condition, vacuum in the circuit on one side of a diaphragm allows atmospheric pressure to apply a force to a valve component or sealing means on the opposite side of the diaphragm; this force is, in turn, counteracted by a spring. Equilibrium is achieved when the sealing means of the regulator shuts off the incoming vacuum at the set-point pressure. Varying the spring tension will increase or decrease the set-point pressure.

As flow increases, suction pressure in the control mechanism is reduced thus allowing the sealing means to move away from the seat to continually meet the flow demand of the patient circuit. The difference in regulated suction between the flowing and static conditions is called spike. Since the sealing means needs to move away from the seat to allow for flow, there must be a corresponding reduction in suction pressure in the patient circuit at a controlled suction pressure. The further the sealing means needs to move from the seat to support the flow required, the lower the regulated pressure will be. It is desirable from a clinical standpoint to minimize spike in the system. A minimum amount of spike allows a caregiver to set the desired clinical suction pressure in either a flowing or static condition and depend on the regulator to maintain the desired suction pressure.

The relationship that defines spike states requires that the resistance to flow is restricted by the geometry of the flow path. To maintain as low a pressure change as possible, the cross sectional area of the conduit should be more than any restriction formed by the sealing means and the seat. When the conduit is a round passage and the restriction is essentially a cylinder, the expression is as follows:

Area of conduit $\geqq$ Area of Restriction $$\frac{\Pi d^2}{4} \geq \Pi dh$$
$$\frac{d}{4} \geq h$$

Where:
    d is the effective diameter of the orifice opening; and
    h is the distance the piston must travel to provide maximal flow, i.e., the linear distance separating the fully-open and fully-closed positions.

Consequently, a control device that permits the travel of the sealing means to one quarter of the conduit diameter will have minimal spike and maximum flow for those dimensions. To achieve d/4 travel against a compensating spring with minimal pressure increase (spike), the actuating diaphragm must be as large as practical to provide the necessary force.

The compensatory airflow in the described submission serves two purposes. The additional airflow along the shaft of the regulator supplements the force on the sealing surface by causing a shear force along the shaft of the piston. This shear force aids in the force on the sealing means. The second effect is that the change in direction of airflow caused by the shield creates a momentum change force as the flow is reversed through the labyrinth shield and applies a force on the sealing means. These two forces are greatest when the difference in pressure between the patient circuit and the atmosphere is greatest. These forces are greatest in a static situation. In a dynamic situation both of these forces decrease as the pressure inside of the circuit decreases. This decrease in force enables the resultant dynamic suction pressure to be closer to the original set point pressure with a reduction in the amount of spike experienced by the system, with a resultant improvement in the performance of the regulator.

One aspect of the present invention provides a barrier to prevent incoming foreign material from adhering to the functional components of the regulator.

In one aspect the barrier is an air curtain.

In a further aspect the barrier is a shroud.

In another aspect the barrier is a diaphragm or a bellows.

In another aspect the barrier is a water or fluid dissipative coating.

In yet a further aspect, the barrier is a combination of all four of the above.

In another aspect of the invention, the regulator can be flushed, without regard for fluid intrusion into critical areas of the control.

A further aspect of the invention provides a controlled air-flow to wash foreign material from the functional components of the regulator.

Another aspect of the invention provides a controlled airflow that allows the vacuum regulation diaphragm to be referenced to atmosphere, while having calibrated one way flow coming across the critical feedback path. This flow is calibrated to a low level in order to have little effect on the regulated vacuum level of the system, but sufficient to discourage the entrainment of contaminants.

Still a further aspect of the invention provides a regulator design which exhibits low spike. This low spike is enhanced by the compensatory effects of a calibrated airflow which counteracts the spike pressure exhibited by a flowing system.

Still a further aspect of the invention provides a regulator design which exhibits low friction and therefore low dead band. This low friction is enhanced by the calibrated airflow which provides an air bearing means.

These and other aspects will become apparent from the following description.

BRIEF DESCRIPTION OF THE DRAWINGS

The invention is best understood from the following detailed description when read in connection with the accompanying drawings. It is emphasized that, according to common practice, the various features of the drawing are not to scale. On the contrary, the dimensions of the various features are arbitrarily expanded or reduced for clarity. Included in the drawing are the following Figures:

FIG. 3b is a cross-sectional view of the insert taken along the lines A-A of FIG. 3a.

FIG. 3c is a side view of the insert of FIG. 3a.

DETAILED DESCRIPTION OF THE INVENTION

Air Curtain Isolation Embodiment

Figure 1:
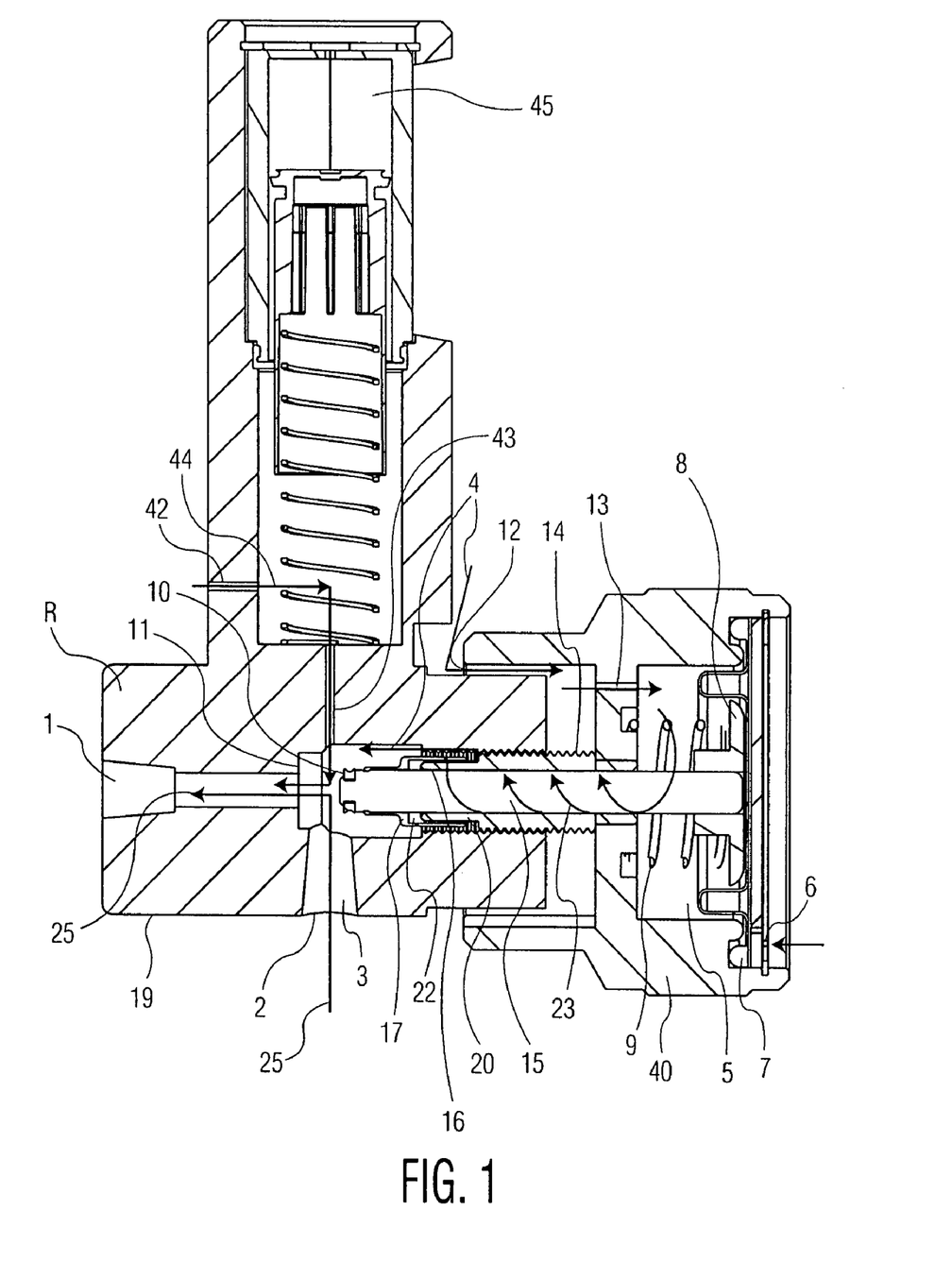
FIG. 1 is a system cross-sectional layout of a complete regulation system that incorporates an air curtain as an isolation for critical components.

Referring to FIG. 1, one exemplary embodiment of a suction regulator R is shown. The suction regulator R includes a body 19 defining an outlet port 1 that is configured to be coupled to a source of suction, an inlet port 2 that is configured to be in fluid communication with a patient via a conduit (not shown), and a fluid passageway 3 defined between the outlet port 1 and inlet port 2. A valve seat 11 is defined along the fluid passageway 3. Although not shown, valve seat 11 may also be a separate component assembled with fluid passageway 3. A valve 15 (also referred to herein as a stem) is movable with respect to valve seat 11 for selectively exposing inlet port 2 to the source of suction to draw fluid flow 25 through inlet port 2 and fluid passageway 3 under the force of suction. The valve 15 optionally includes a seal 10 for sealing contact with valve seat 11.

In one exemplary use of the suction regulator R illustrated in FIG. 1, unregulated hospital central suction is applied to regulator R through outlet port 1 drawing fluid 25 through the inlet port 2 connected to the patient. The reduction in pressure (i.e., increase in suction) in fluid passageway 3 also encourages airflow 4 (depicted by arrows) through a gap 12 provided between body 19 and housing 40. The housing 40 is threadedly engaged onto body 19 and moveable with respect thereto. Although not shown, housing 40 and body 19 may be integral components.

Airflow 4 is drawn through an orifice 13 and into a regulating chamber 5. The regulating chamber 5 is defined in the housing 40. In operation, regulating chamber 5 maintains a reduced pressure signal. This reduced pressure signal is possible since the clearance afforded by air gap 16 formed by the clearance between the outer diameter of stem 15 and the inner diameter of threaded sleeve 14 is sufficiently larger than the open area of orifice 13.

Diaphragm 7 is positioned between regulating chamber 5 and atmospheric reference 6. The reduction in pressure in regulating chamber 5 causes diaphragm 7 to exert a force against piston 8 urging valve 15 toward valve seat 11. Counterbalancing the force of the diaphragm is the force of a resilient element 9, which may optionally be a spring. Diaphragm 7 will continue to move until equilibrium has been reached with the spring force exerted by resilient element 9. In the process of moving piston 8, seal 10 translates toward or in contact with seat 11 to stop the reduction in pressure caused by outlet port 1. Regulated suction is then delivered to the patient connection P via inlet port 2.

The arrangement of valve 15, valve seat 11, resilient element 9, piston 8 and diaphragm 7 of the suction regulator R may also be referred to herein as a means for regulating suction within the fluid passageway 3. It should be understood by one skilled in the art that alternative means exist for regulating suction within a fluid passageway. Accordingly, the invention is not limited to the above arrangement of components.

The suction output of the regulator is varied by changing the relative position of the housing 40 by rotating the housing 40 along at least a portion of the length of the threaded sleeve 14, thus changing the load on resilient element 9 and consequently translating the valve 15 with respect to the valve seat 11.

The flow requirements of inlet port 2 will affect the negative pressure signal in the fluid passageway 3, thus influencing the reduced pressure in regulating chamber 5. This change in pressure will in turn effect the movement of seal 10 in relation to valve seat 11.

Airflow 4 through orifice 13 continuously washes the internal surfaces of regulating chamber 5 when the valve 15 is separated from the valve seat 11. This airflow 4 travels between threaded sleeve 14 and valve 15 to provide a clean wash of air in gap 16.

Mechanical barrier 17, also referred to herein as a shroud, protects the exposed surfaces of valve 15 when any foreign material is propelled into inlet port 2 with velocity sufficient to enter this area. For proper regulation, valve 15 slides freely, i.e., without significant resistance, within the interior of threaded sleeve 14. Any material buildup of foreign material on the interface of the mating surfaces of the valve 15 and sleeve 14 would impede free relative motion of the valve 15. Threaded sleeve 14 contains a smaller diameter section 20 which allows for the full range of motion between valve 15 and threaded sleeve 14, minimizing the possibility of exposing the interface of these two parts to the ingress of foreign materials. The open area between barrier 17 and the smaller diameter section 20 is similar to the open area of the air gap between valve 15 and threaded shaft 14. This similarity of areas ensures a consistent one way purging airflow 4 providing for only clean air to travel in these air spaces. Although not shown, a filter, such as a felt ring, may be included in the regulator R to filter the airflow to minimize airborne particles.

As parts 7, 8, 10 and 15 are acted upon by the relative pressure changes in regulation chamber 3; volume in regulating chamber 5 will increase and decrease causing the potential for airflow 4 to reverse direction. Calibrated airflow 4 through gap 16 is sufficiently great enough to offset the speed of movement of parts 7, 8, 10 and 15 thereby making it possible to ensure airflow 4 only provides a one way wash of clean air over these components. The regulating means is preferably defined by parts 5, 6, 7, 9, 10, 11, 15.

Additionally, the airflow 23 along the outer diameter of the valve 15 functions as an air bearing to minimize sliding friction.

In a static condition, with little flow demands from patient P via inlet port 2, the force of seal 10 upon seat 11 is aided by the shear of airflow 23 along shaft 15. The force of seal 10 upon seat 11 is also aided by the reversal of direction of airflow 23 as impact head on face 22. These two additional forces acting upon -seal 10 help counteract the change in regulated pressure, spike or droop, as flow varies with change in the demands from patient P upon the system.

The regulator R includes a means 45 for indicating a level of suction within fluid passageway 3. The suction indication means 45 may be a pressure gauge 45 mounted to body 19, for example, as illustrated in FIG. 1. Two orifices 42 and 43 formed in body 19 permit the introduction of atmospheric airflow 44 through gauge 45 and into fluid passageway 3 under the source of suction. In operation, normal variation in the level of regulated suction will result in changes in the gauge reading of gauge 45. Movement of gauge 45 is caused by changes in the relative volume of air in gauge 45. Reduction in volume of the airspace causes atmospheric air to enter fluid passageway 3, while increases in volume of this airspace causes atmospheric air to enter gauge 45.

Diaphragm Isolation Embodiment

Figure 2:
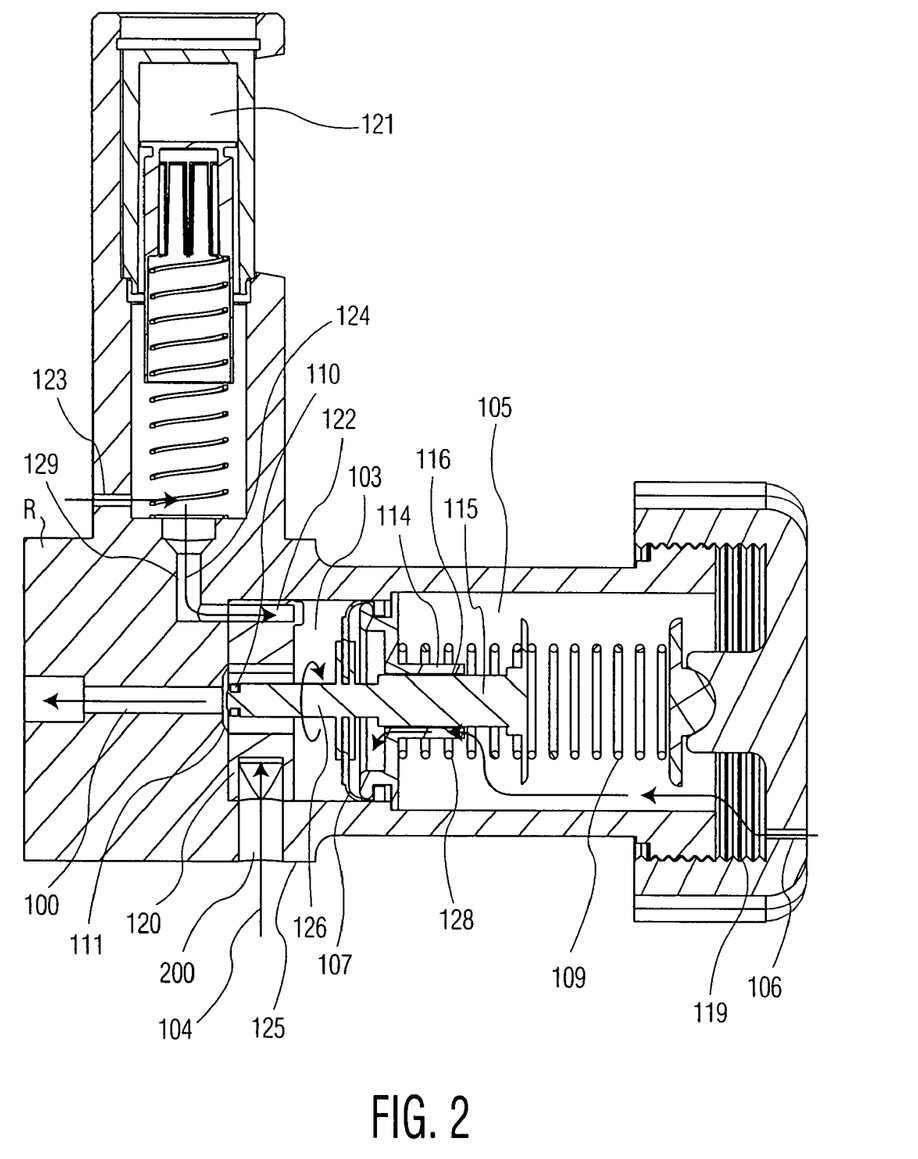
FIG. 2 is a system cross-sectional layout of a complete regulation system that incorporates diaphragm as an isolation for critical components.

Another exemplary embodiment of a suction regulator is illustrated in FIG. 2. According to this exemplary embodiment, the regulator R includes a body 125 defining an outlet port 100 that is configured to be coupled to a source of suction (not shown), an inlet port 200 that is configured to be in fluid communication with the patient (not shown), and a fluid passageway 103 defined between outlet port 100 and inlet port 200. A valve seat 111 is defined along or positioned within fluid passageway 103. A valve 126 is movable with respect to valve seat 111 for exposing inlet port 200 to the source of suction. The valve 126 optionally includes a seal 110 at its sealing end for mating with valve seat 111.

An insert 120 is positioned within fluid passageway 103 for directing fluid flow 104 into fluid passageway 103. The insert 120 includes a helical channel for promoting centrifugal separation of the particles and aerosols of fluid flow 104 within fluid passageway 103, as best described with reference to FIGS. 3*a*-3*c*. The insert 120 further comprises an air passageway 122 that is positioned in fluid communication with means 121 for indicating a level of suction within fluid passageway 103. The suction indication means 121 may be a pressure gauge 121 mounted to body 125, for example, as illustrated in FIG. 2. The suction indication means could also be an analog gauge known in the art comprised of a copper bellows.

Similar to the previous embodiment, two orifices 123 and 129 formed in body 125 permit the introduction of atmospheric airflow 124 through gauge 121 and into fluid passageway 103 under the source of suction. In operation, normal variation in the level of regulated suction will result in changes in the gauge reading of gauge 121. Movement of gauge 121 is caused by changes in the relative volume of air in gauge 121. Reduction in volume of the airspace causes atmospheric air to enter fluid passageway 103, while an increase in volume of this airspace causes atmospheric air to enter gauge 121. In prior art suction regulators, an increase in volume of the gauge 121 would draw fluid from passageway 103 and the patient circuit into gauge 121, consequently introducing contaminants into the pressure gauge. Thus, the benefit afforded by an isolation means may also be applied to the suction indication means of the device as well.

The air passageway 122 of insert 120 faces downstream of the fluid flow 104 to minimize entrainment of fluids into the gauge 121. Insert 120 may be constructed to be removable and replaceable in the event of fluid intrusion to simplify any necessary cleaning processes. Furthermore, gauge 121 is oriented in a vertical self-draining orientation to facilitate cleansing and flushing. The introduction of atmospheric air into orifice 123 allows for any increase in the volume of gauge 121 to be made up of clean atmospheric air, as opposed to air from the patient circuit.

The valve 126 is positioned through an aperture (not shown) provided in a diaphragm 107. Diaphragm 107 is positioned between fluid passageway 103 and atmospheric reference 106. The diaphragm 107 is adapted to flex in response to a pressure differential on its opposing sides between fluid passageway 103 and atmospheric reference 106, as should be understood by one skilled in the art. The valve 126 is coupled to diaphragm 107, such that flexion of diaphragm 107 induces translation of valve 126 with respect to valve seat 111.

Flexion of the diaphragm is counterbalanced by a spring loaded piston 115, extending from, or mounted to, valve 126. The spring loaded piston 115 is positioned within a regulating chamber 105. The diaphragm 107 separates fluid passageway 103 from regulating chamber 105 to prevent or limit deleterious fluid from entering regulating chamber 105 and contaminating the components positioned within chamber 105, including spring loaded piston 115. In another exemplary embodiment not illustrated herein, the diaphragm and spring arrangement shown in FIG. 2 may be replaced by a bellows.

A first resilient element 128 (in the form of a spring, for example) biases piston 115 and valve 126 in a direction away from valve seat 111. A second resilient element 109 (in the form of a spring, for example) that is positioned on the opposite side of piston 115, removes the preload of first resilient element 128 for biasing piston 115 and valve 126 in a direction toward valve seat 111. An adjustable threaded sleeve 119 is rotatably coupled to body 125 for adjusting the compression force of second resilient element 109 against piston 115.

The arrangement of valve 126, valve seat 111, resilient elements 128 and 109, piston 115 and diaphragm 107 of the suction regulator R may also be referred to herein as a means for regulating suction within the fluid passageway 103. It should be understood by one skilled in the art that alternative means exist for regulating suction within a fluid passageway. Accordingly, the invention is not limited to the above arrangement of components.

According to one exemplary use of the suction regulator R illustrated in FIG. 2, unregulated wall suction enters regulator R through inlet port 100. Fluid passageway 103 undergoes a reduction in pressure encouraging fluid flow 104 (depicted by arrows) through inlet port 100. Fluid flow 104 relays the reduced pressure signal to regulating chamber 105 via diaphragm 107. This reduced pressure signal is possible since a diaphragm will transmit a change in pressure with low resistance and the clearance afforded by air gap 116 formed by the clearance between the outer diameter of valve 115 and the inner diameter of sleeve 114 allows motion of the valve. The clearances provide the performance attributes previously described for an air curtain isolation. The reduction in pressure in chamber 105 causes diaphragm 107 to exert a force against piston 115. Counterbalancing the force of the diaphragm is the force of resilient element 128, which may optionally be a compression spring. Diaphragm 107 will continue to move until equilibrium has been reached with the force exerted by resilient element 128.

In the process of moving piston 115, seal 110 should preferably come in to contact with seat 111 to stop the reduction in pressure caused by high negative pressure at outlet port 100. Regulated suction is then delivered to the patient via inlet port 200. The suction output is varied by changing the relative position of the spring seat by rotating the threaded sleeve 119, thus changing the load on resilient element 109, as described previously.

The flow requirements of inlet port 200 will affect the negative pressure signal in fluid passageway 103 thus influencing the reduced pressure in chamber 105. This change in pressure will in turn effect the movement of seal 110 in relation to seat 111.

Figure 3A:
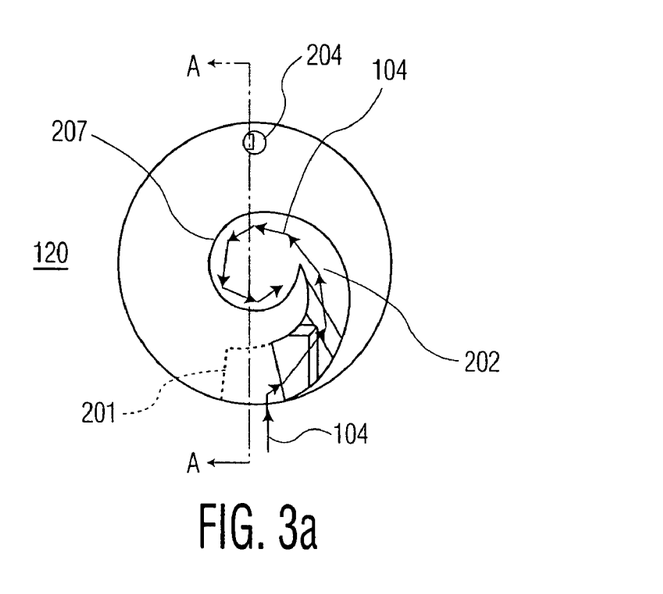
FIG. 3a is a top plan view of the insert of FIG. 2.
Figure 3B:
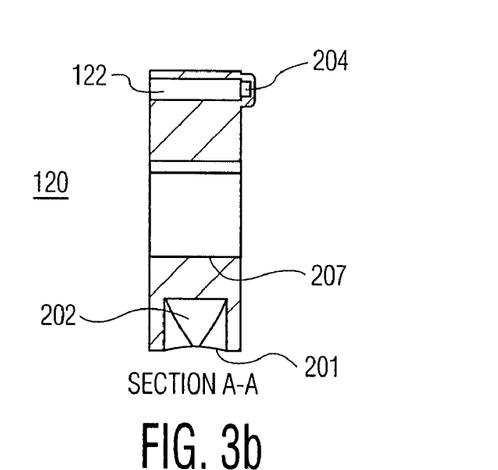
Figure 3C:
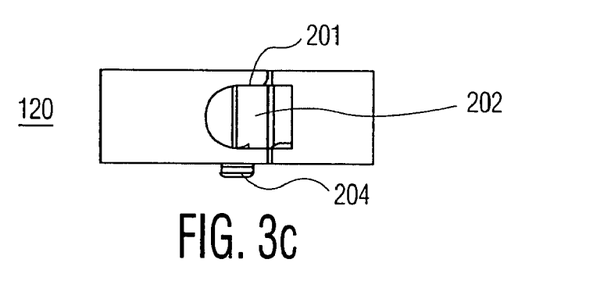

Referring to the FIGS. 3a-3c, detailed views of insert 120 of FIG. 2 are illustrated. FIG. 3a is a top plan view of insert 120. The insert 120 includes an inlet 201 (shown in broken lines) for receiving fluid flow 104 from inlet port 200 that is connected to the patient. Fluid flow 104 travels through a helical channel 202 that extends between inlet 201 and thru-hole 207. Although not shown in this view, valve 126 is slideably positioned through thru-hole 207 (see FIG. 2). The helical channel 202 promotes centrifugal separation of the particles and aerosols of fluid flow 104 within fluid passageway 103, as previously described above.

FIG. 3b is a cross-sectional view of insert 120 taken along the lines A-A of FIG. 3a. As best shown in this view, air passageway 122 is disposed along the height dimension of insert 120. The air passageway 122 is positioned in fluid communication between fluid passageway 103 and pressure gauge 121. An orifice 204 is defined at the end of air passageway 102 for delivering atmospheric air into fluid passageway 103.

FIG. 3c is a side view of insert 120 of FIG. 3a illustrating inlet 201 of helical channel 202.

Figure 4:
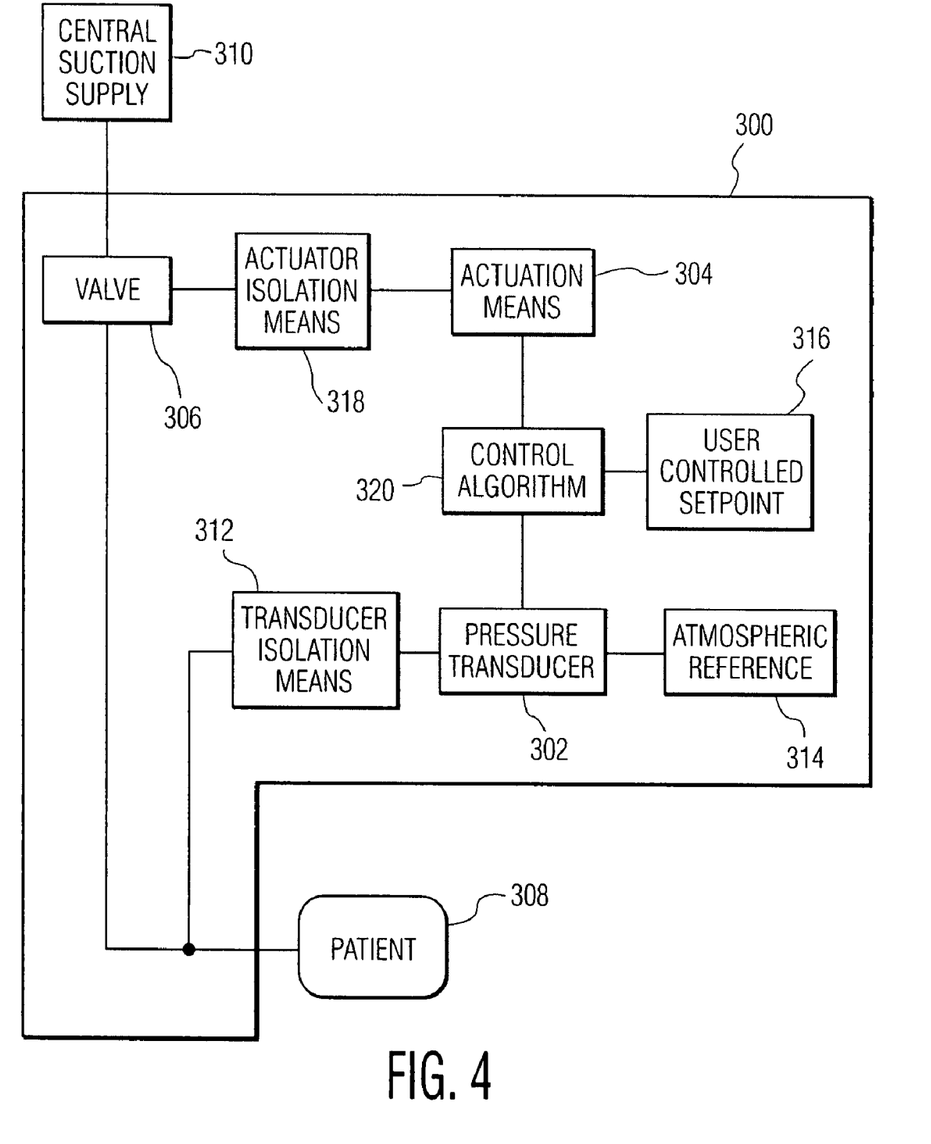
FIG. 4 is a block diagram of an exemplary electric suction regulator system.

According to another aspect of the invention, the suction regulator may be an electric suction regulator 300, as shown schematically in FIG. 4. An electric suction regulator 300 may be comprised of a pressure transducer 302 to sense the level of suction in the circuit, and an actuation means 304, such as a motor or solenoid, to power a valve 306 that adjusts the flow of suction delivered to the patient 308 from the central suction supply 310. The actuation means 304 operatively turns the source of suction on and off in response to downstream conditions in the circuit, as determined by a control algorithm 320.

Similar to the prior embodiments disclosed herein, the means for regulating suction within the fluid passageway is isolated from the fluid passageway of the regulator. Specifically, one side of the pressure transducer 302 may be isolated from contaminants in the fluid flow delivered by the patient 308 by means of an transducer isolation means 312, such as an elastomeric member, or low durometer elastomeric covering. The opposing side of the pressure transducer 302 may be referenced to atmospheric air 314, as shown. Given the construction of silicon wafer based pressure transducers, minimal displacement is needed to determine a change in pressure, and fluid flow based on this displacement is negligible.

The actuation means 304 may be isolated from the fluid path by an actuator isolation means 318. The actuator isolation means 318 may be a diametric seal, elastomeric film, o-ring, u-cup or a wiper seal positioned over the shaft of the actuation means 304 (e.g., motor), for example. In this way the power of the actuation means 304 would not be adversely affected by the presence of contaminants in the patient circuit. The actuation means 304 in turn could adjust the flow of the circuit in a variety of means.

The control algorithm 320 compares user controlled setpoint 316 with the level of suction in the circuit in the regulator (as determined by the pressure transducer 302). The flow of suction delivered to the circuit may be adjusted via actuation means 304 according to the computations of control algorithm 320. The control of the actuation means 304 can be via linear approximation of a seal to a seat, as in the mechanical analog, or alternatively may be achieved with a solenoid type valve displaying simple ON/OFF control, in concert with a PWM signal to regulate the intended output.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A suction regulator for regulating suction withdrawal of body fluids from a patient, the suction regulator comprising:
   a body;
   an outlet port defined in said body that is configured to be coupled to a source of suction;
   an inlet port defined in said body that is configured to be in fluid communication with the patient;
   a fluid passageway defined between the outlet port and the inlet port;
   a means for regulating suction at least partially positioned within the fluid passageway for maintaining a desired level of suction within the fluid passageway, wherein in an open position of the regulating means fluid can travel in the fluid passageway between the inlet port and the outlet port under the source of suction, and in a closed position of the regulating means the regulating means substantially prevents fluid from travelling in the fluid passageway between the inlet port and the outlet port; and
   a means for introducing atmospheric air into at least a portion of the fluid passageway, over the regulating means and through the outlet port under the source of suction when the regulating means is maintained in the open position.

2. The suction regulator of claim 1, wherein the ratio of volume of atmospheric air delivered through the fluid passageway to the total volume of fluid delivered through the passageway is greater than or equal to 0.001:1.0.

3. The suction regulator of claim 1, further comprising means for measuring a level of suction within said fluid passageway.

4. The suction regulator of claim 3, further comprising means for introducing atmospheric air into said measuring means.

5. The suction regulator of claim 4, wherein said introducing means is disposed within said body.

6. The suction regulator of claim 4, wherein said introducing means comprises an orifice that is positioned in fluid communication with atmospheric air and the fluid passageway.

7. The suction regulator of claim 1, further comprising a regulating chamber separate from the fluid passageway, wherein the regulating means are at least partially positioned within the regulating chamber.

8. The suction regulator of claim 7, wherein means for introducing atmospheric air fluid communication with the regulating chamber and the fluid passageway.

9. The suction regulator of claim 8, wherein means for introducing atmospheric air comprises an orifice defined in the regulator.

10. The suction regulator of claim 8, wherein the regulating means comprises a valve seat defined along the fluid passageway and a moveable valve for selectively mating with said valve seat.

11. The suction regulator of claim 10, wherein the atmospheric air is delivered over a surface of the valve and into at least a portion of the fluid passageway.

12. The suction regulator of claim 10, further comprising a shroud positioned over at least a portion of the valve for limiting exposure of the valve to fluid delivered through the fluid passageway.

13. The suction regulator of claim 10, wherein the regulating means further comprises a diaphragm for biasing the valve with respect to the valve seat.

14. The suction regulator of claim 13, wherein the regulating means further comprises a resilient element for counterbalancing the force exerted upon the valve by the diaphragm.

15. In a suction regulator comprising an outlet port coupled to a source of suction, an inlet port in fluid communication with a patient, a fluid passageway defined between the outlet port and the inlet port, and means for regulating the level of suction within the fluid passageway, a method of operating the suction regulator comprising:
   exposing the inlet port to the source of suction;
   biasing the regulating means to an open position;
   drawing fluid through the inlet port, into the fluid passageway and through the outlet port under the source of suction;
   drawing atmospheric air under the source of suction (i) into a regulation chamber that is separate from the fluid passageway, (ii) over the regulating means and (iii) through the fluid passageway, to limit the flow of fluid into the regulation chamber when the regulating means is biased to an open position; and
   biasing the regulating means to a closed position to substantially prevent fluid and atmospheric air from travelling in the fluid passageway between the inlet port and the outlet port of the suction regulator.

16. The method of claim 15, said step of drawing atmospheric air further comprising receiving the atmospheric air from an orifice defined along or within the regulator under the source of suction.

17. A suction regulator comprising:
   a body;
   an outlet port defined in said body that is configured to be coupled to a source of suction;
   an inlet port defined in said body that is configured to be in fluid communication with the patient;
   a fluid passageway defined between the outlet port and the inlet port, a means for regulating suction at least partially positioned within the fluid passageway for maintaining a desired level of suction within the fluid passageway, wherein in an open position of the regulating means fluid can travel in the fluid passageway between the inlet port and the outlet port under the source of suction, and in a closed position of the regulating means the regulating means substantially prevents fluid from travelling in the fluid passageway between the inlet port and the outlet port;

means for measuring a level of suction within said fluid passageway, wherein at least a portion of said measuring means is positioned within said body, and means for introducing atmospheric air through said measuring means and into said fluid passageway under the source of suction to limit the introduction of fluid into said measuring means.

18. The suction regulator of claim 17, wherein said introducing means comprises an orifice that is positioned in fluid communication with atmospheric air and the fluid passageway.

19. A device for regulating suction withdrawal of body fluids from a patient, the device comprising:

an outlet port that is configured to be coupled to a source of suction;

an inlet port that is configured to be in fluid communication with a patient;

a fluid passageway defined between the outlet port and the inlet port;

a valve seat defined on or along the fluid passageway;

a moveable valve for selectively mating with said valve seat, wherein in an open position of the device the valve is separated from the valve seat such that fluid can travel through the fluid passageway between the inlet port and the outlet port under the source of suction, and wherein in a closed position of the device the valve is mated with the valve seat such that fluid is substantially prevented from travelling through the fluid passageway between the inlet port and the outlet port under the source of suction;

a regulating chamber in fluid communication with the fluid passageway;

a diaphragm positioned in said regulating chamber for biasing the valve with respect to the valve seat; and an atmospheric air passageway defined within the device, wherein said atmospheric air passageway is positioned for the delivery of atmospheric air into the regulating chamber, along a surface of the valve, into the fluid passageway and through the outlet port under the source of suction to limit the introduction of fluid into the regulating chamber when the device is maintained in the open position.

\* \* \* \* \*